United States Patent
Yang et al.

(10) Patent No.: US 12,312,519 B2
(45) Date of Patent: May 27, 2025

(54) PREPARATION METHOD FOR MULBERRY SILK THAT FLUORESCES UNDER NEAR-INFRARED LIGHT AND PRODUCT

(71) Applicant: ZHEJIANG UNIVERSITY, Hangzhou (CN)

(72) Inventors: Mingying Yang, Hangzhou (CN); Jie Wang, Hangzhou (CN); Yuyin Chen, Hangzhou (CN); Ying Zhang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 824 days.

(21) Appl. No.: 17/622,770

(22) PCT Filed: Jun. 23, 2020

(86) PCT No.: PCT/CN2020/097679
§ 371 (c)(1),
(2) Date: Dec. 24, 2021

(87) PCT Pub. No.: WO2020/259490
PCT Pub. Date: Dec. 30, 2020

(65) Prior Publication Data
US 2022/0272956 A1 Sep. 1, 2022

(30) Foreign Application Priority Data
Jun. 26, 2019 (CN) .......................... 201910558728.9

(51) Int. Cl.
*C09K 11/02* (2006.01)
*A23K 20/147* (2016.01)
*B82Y 99/00* (2011.01)
*C09K 11/77* (2006.01)

(52) U.S. Cl.
CPC .......... *C09K 11/025* (2013.01); *A23K 20/147* (2016.05); *B82Y 99/00* (2013.01); *C09K 11/7766* (2013.01)

(58) Field of Classification Search
CPC .............. C09K 11/025; C09K 11/7766; A23K 20/147; B82Y 99/00
See application file for complete search history.

(56) References Cited

FOREIGN PATENT DOCUMENTS

| CN | 110367209 A | 10/2019 | |
| WO | WO-2014011118 A1 * | 1/2014 | ............. A61K 47/02 |

OTHER PUBLICATIONS

Tansil et al. Functional Silk: COlored and Luminescent. Adv. Mater., 2012, 24, 1388-1397.*
Iizuka et al. Colored Fluorescent Silk Made By Transgenic Silkworms. Adv. Funct. Mater. 2013, V. 23, pp. 5232-5239.*
Wang et al. Different EDC/NHS Activation Mechanisms between PAA and PMAA Brushes and the Following Amidation Reactions. Langmuir, 2011, V. 27, pp. 12058-12068.*
Yokoyama et al. (Lipid transfer particle from the silkworm, Bombyx mori, is a novel member of the apoB/large lipid transfer protein family. Journal of Lipid Research. V. 54, 2013, pp. 2379-2381.*
CN201910558728.9—First Office Action mailed on Mar. 9, 2020, 10 pages.
CN201910558728.9—Notice of Grant mailed on May 14, 2020, 5 pages.
PCT/CN2020/097679—International Search Report and Written opinion mailed on Sep. 21, 2020, 18 pages.

* cited by examiner

*Primary Examiner* — Amina S Khan
(74) *Attorney, Agent, or Firm* — Getech Law LLC; Jun Ye

(57) ABSTRACT

Disclosed is a method for constructing fluorescent *Bombyx Mori* silkworm silk irradiated by near-infrared light and its products, comprising: (1) preparing upconversion nanoparticles, and performing surface modification with concanavalin to obtain modified upconversion nanoparticles; (2) uniformly dispersing the modified upconversion nanoparticles in water to formulate an aqueous solution of the upconversion nanoparticles, (3) picking mature mulberry leaves, immersing the mulberry leaves in the aqueous solution system of the nanoparticles, leaching water, and naturally drying the mulberry leaves; (4) after silkworms have grown for a set time, feeding the treated mulberry leaves to the silkworms until the silkworms spin silk cocoons; and (5) collecting the silk, so as to obtain mulberry silk that fluoresces under near-infrared light. The present invention selects upconversion nanoparticles capable of emitting fluorescence under the irradiation of near-infrared light which has stronger penetration, thus has better application in deep tissue imaging.

12 Claims, 1 Drawing Sheet

PREPARATION METHOD FOR MULBERRY SILK THAT FLUORESCES UNDER NEAR-INFRARED LIGHT AND PRODUCT

CROSS REFERENCE TO RELATED APPLICATIONS

This application is a 371 of International Application No. PCT/CN2020/097679, filed Jun. 23, 2020, which claims priority to foreign application, Chinese Application No. 201910558728.9, filed Jun. 26, 2019. The contents of each of the above-captioned patent applications are hereby expressly incorporated herein by reference in their entireties.

TECHNICAL FIELD

The present invention belongs to the field of silk fiber production and processing, and particularly relates to a preparation method for Bombyx mori silkworm silk that fluoresces under near-infrared light.

BACKGROUND

Silk fiber is usually rewarded with a title of "fiber queen". Silk fiber has excellent mechanical properties; Fabric made of silk fiber has a smooth hand feeling and bright color, and has good air permeability and heat insulation property. Therefore, silk fiber plays an important role in the development history of China's economy. However, with the rapid development in the industrialized synthetic technology of artificial fiber, the traditional silkworm textile industry is facing serious challenges. In recent years, there are more and more concerns on the studies of modification of natural silk. Researchers have introduced functionalized macromolecules into silk fiber or modified fiber with macromolecules to improve the properties of silk fiber and promote its application value. At present, there are studies on transforming natural silk into fluorescent silk fiber to be applied into in vivo imaging and detection. However, it is found that common silk fiber has very strong autofluorescence when used, and may emit yellow and red fluorescence under the exposure of a purple light and green light, respectively, seriously disturbing the detection application. On the other hand, the fluorescence of was obtained currently under the excitation condition of visible lights; but visible light has poor penetration properties and hardly reaches to in vivo deep tissues; and the excited fluorescence is very easily quenched to limit its application in in vivo living imaging. Therefore, it is extremely important to seek for a suitable method to modify silk fiber for practical values.

Upconversion nanoparticles is a kind of luminophor constituted by rare earth ions, and may transform long-wavelength near-infrared light into short-wavelength visible light, and gives out light stably and has a high signal to noise ratio. Compared with common luminescent materials, such as, anthocyanins and quantum dot particles, the upconversion nanoparticles has stable properties, low biotoxicity, and high illumination intensity and thus, is extensively applied in biomedicine test and imaging fields. Therefore, the upconversion nanoparticles are combined with silk fiber for fiber modification, which may enhance the practical feasibility of silk fiber in in vivo imaging and detection fields. In the prior art, the upconversion nanoparticle is mixed with regenerated fibroin and prepared into luminous silk fiber by electrostatic spinning. However, electrostatic spinning takes long time, and has low yield, and is incapable of achieving batch production. Furthermore, some technologies have been used for the surface modification on upconversion nanoparticles, but the surface modified upconversion nanoparticles are always not distributed evenly and fall off very easily. Therefore, it is necessary to design and develop a simple novel method for obtaining the upconversion nanoparticles in volume production, thus preparing the mulberry silk that fluoresces under near-infrared light.

SUMMARY

To overcome the low fluorescence specificity, weak penetrating of excitation light, and difficult imaging and detection application and other defects existing in the prior art of fluorescent silk preparation, the present invention provides a method for creating fluorescent Bombyx mori silkworm silk irradiated by near-infrared light. The method can not only improve the fluorescence intensity, penetrating power and biocompatibility of the fluorescent silk fiber, but also be suitable for mass production, free of environmental pollution.

A method for creating fluorescent Bombyx mori silkworm silk irradiated by near-infrared light, including the following steps:

(1) preparing upconversion nanoparticles, and performing surface modification with concanavalin to obtain modified upconversion nanoparticles;

(2) uniformly dispersing the modified upconversion nanoparticles from step (1) into water to formulate an aqueous solution of the upconversion nanoparticles;

(3) picking mature mulberry leaves, immersing the mulberry leaves in the aqueous solution system of the nanoparticles in the step (2), fishing out and leaching water, and naturally drying the mulberry leaves;

(4) after silkworms have grown for a set time, feeding the treated mulberry leaves in the step (3) to the silkworms until the silkworms spin silk cocoons; and (5) collecting the silk to obtain mulberry silk that fluoresces under near-infrared light.

In this present invention, a flat board may be used to induce silkworms to spin on the board or silk reeling is performed after cocooning on the clusters thereon; such two methods can obtain the mulberry silk that fluoresces under near-infrared light. Finally, the fluorescent modified mulberry silk under infrared irradiation is obtained, and can be applied in medical and biological fields for in vivo imaging and detection analysis.

Preferably, the upconversion nanoparticles have a core-shell structure. Experimental results show that the upconversion nanoparticles with core-shell structure have higher fluorescence intensity (as shown in FIG. 1).

Preferably, a polyacrylic acid (PPA)-modified core-shell structure upconversion nanoparticles may be selected in this present invention.

The present invention synthesizes and prepares the PPA-modified core-shell structure upconversion nanoparticles, including the following steps: introducing concanavalin (ConA), then grafting the concanavalin on the surface of the upconversion nanoparticles by means of a cross-linking agent 1-ethyl-3-(3-dimethylaminopropyl)-carbonimide to form a composite co-polymer. A method for preparing the PPA-modified core-shell structure upconversion nanoparticles is as follows:

Core-shell structure upconversion nanoparticles ($\beta$-NaYF$_4$:Yb,Er@$\beta$-NaYF$_4$) are prepared with an existing method, and dispersed into a n-hexane solution. Polyacrylic acid (PAA) is grafted on the surface of nanoparticles by a ligand exchange method; 1 mL upconversion nanoparticle solution and 5 mL dimethyl formamide (DMF) are blended, and then 4 mL n-hexane is added followed by stirring for 3 h. 5-10 mL isopropanol is added for precipitation, and precipitates are washed by DMF for several times. The precipitates are resuspended in PAA/DMF solution (PAA concentration is 10 mg/mL (5-10 mL), staying over the night, stirred, centrifuged and washed.

Preferably, the method of surface modification with concanavalin is as follows:

10 mg PAA-modified nanoparticles are taken and dispersed into 1 mL aqueous solution; 1 mg EDC and NHS are respectively added and stirred for reaction for 3-6 h, afterwards, 30 uL concanavalin aqueous solution (3-10 mg/mL) is added and stirred over the night, centrifuged and washed to obtain concanavalin-modified upconversion nanoparticles.

Preferably, the upconversion nanoparticles used in the present invention include but not limited to $\beta$-NaYF$_4$:Yb, Er@$\beta$-NaYF$_4$ upconversion nanoparticles. Further, other preparation methods may be used to obtain the following NaGdF$_4$:Yb/Er@NaGdF$_4$:Yb/Nd or shell structure-free NaYF$_4$:Yb,Er or upconversion nanoparticles emitting red fluorescence and the like.

Preferably, the above aqueous solution of the upconversion nanoparticle has a concentration of 1-5 g/L.

The silkgland cells of silkworms begin to enlarge from the third day of fifth-instar stage; most of the digested mulberry leaves are converted to synthesize fibroin, and before this, mulberry leaves are only nutrition required by growth or excreted. To improve the feeding efficiency, preferably, the silkworms are fed with the mulberry leaves in the step (3) after growing to the third day of fifth-instar stage. Silkworms in the 1st-4th-instar stages are fed with common mulberry leaves.

Preferably, the modified upconversion nanoparticles obtained in the step (1) have a mean diameter of 50-100 nm. The color of the emitted light may be green, red or yellow or the like.

Compared with the conventional way of spraying mulberry leaves, the processing way of mulberry leaves in the step (3) is extraction and airing treatment, such that nanoparticles can be distributed on the front and back surfaces of mulberry leaves more evenly for effective comparative analysis, which avoids the shortcoming of uneven distribution of traditional spraying way. Moreover, the concentration quantification treatment is more precise, thus improving the intake efficiency of silkworm. Preferably, in the step (3), the immersion time of the mulberry leaves is 2-5 min.

Preferably, in the step (5), silkworms are induced to spin on a flat board, thus collecting silk. The obtained silk may be directly used for practical use.

In this invention, concanavalin in the step (1) is a kind of tetramer globulin, and can precipitate multiple saccharides including glucan and fructosan as well as immune globulins, blood-group substances and other multiple glycoproteins, and can bind or reacted with multiple cells. By introducing concanavalin-modified upconversion nanoparticles, the present invention aims at improving cell affinity of nanoparticles with silkworm in vivo, thus participating in the synthesis of fibroin more effectively to form fluorescent silk fiber.

The upconversion nanoparticles prepared in the step (2) are hydrophilic, and thus have good dispersibility in aqueous solution system.

A *Bombyx mori* silkworm silk that fluoresces under near-infrared light is characterized in that the fluorescing mulberry silk is obtained by the preparation method of any of the preceding technical solutions.

The present invention may perform fluorescence detection by near-infrared light excitation, and moreover may detect the content of rare earth elements constituting UCNPs in nanofibers by inductively coupled plasma-mass spectrometry (ICP-MS).

The upconversion material is selected in the present invention, and the upconversion material has longer light stability relative to the shortcomings of being quenched more easily and short maintenance time of fluorescence of the conventional sodium fluorescein.

For the conventional feeding methods, such as, single feeding of rhodamine, sodium fluorescein and other fluorescent chemicals, the produced fluorescence is always distributed into sericin protein, but hardly appears in silk fibroin. So the fluorescence disappears after degumming. In this present invention, the modification of concanavalin may enhance the affinity between feeding materials and silkgland cells, thus improving the fluorescent effect of silk fibroin.

Concanavalin is added and introduced herein for modification to improve the binding of nanoparticles in silkworm in vivo to fibroin and make up the defects of the conventional feeding method, namely, less targeted particles in produced fluorescent silk and poor effect.

The present invention discloses a preparation method for mulberry silk that fluoresces under near-infrared light. At present, there is no simple process to obtain a mulberry silk fluorescing under infrared excitation directly. In this present invention, core-shell structure upconversion nanoparticles are prepared firstly and subjected to surface modification with concanavalin to obtain a nanoparticle co-polymer; then the upconversion nanoparticles are dispersed into water and prepared into aqueous solution having a concentration of 1-5 g/L; fresh mulberry leaves are immersed into the nanoparticle aqueous solution for 2-5 min, and fished out and dried naturally, then silkworms are fed with the mulberry leaves treated by the nanoparticles after growing to the the third day of fifth-instar stage until spinning and cocooning; and the modified mulberry silk is obtained by plat board induction or silkworm cocoon reeling. After being excited by near-infrared light (wavelength: 980 nm), the modified mulberry silk can give off different colors of bright fluorescences, capable of being used for in vivo imaging observation and effective detection of biomolecules.

Compared with the prior art, the present invention has the following distinctive advantages:

(1) The present invention uses upconversion nanoparticles as a feeding preparation. Compared with other fluorescent quantum dot feeding treatment, the upconversion nanoparticles can fluoresce under near-infrared light with stronger penetrating power and thus, has better application to deep tissue imaging. Moreover, compared with fluorescent quantum dots, the upconversion nanoparticles have more stable properties, higher biological safety, stronger signal-to-noise ratio, and a wider application range.

(2) The present invention introduces concanavalin for modification to improve the binding of nanoparticles in silkworm in vivo to fibroin and make up the defects of the conventional feeding method, namely, less targeted particles in the produced fluorescent silk and poor effect.

(3) The present invention uses an extraction method to treat the feeding mulberry leaves such that the nanoparticle coverage is more even, and effective quantitative comparison can be performed.

DETAILED DESCRIPTION OF THE EMBODIMENTS

The present invention will be further described below in detail by the examples; the following examples are used to explain the present invention but not constructed as limiting the present invention.

Examples of the present invention are as follows:

Example 1

Figure 1:
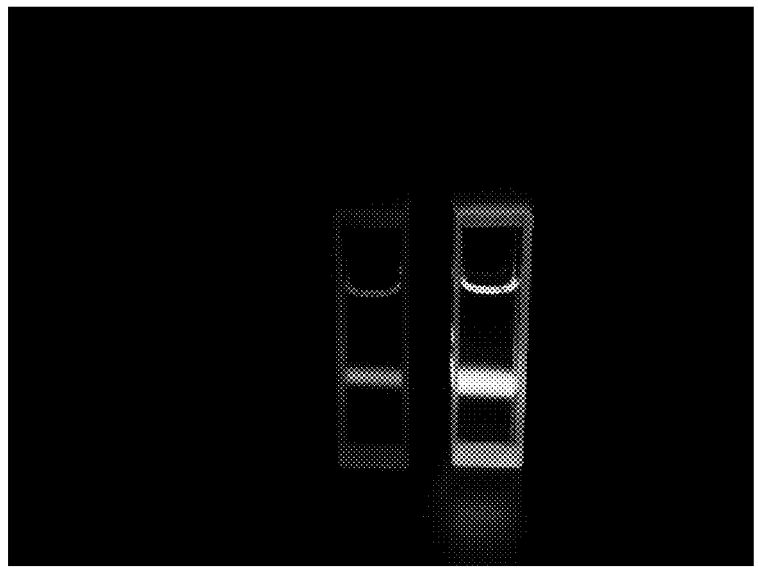
FIG. 1 shows fluorescent pictures of non-core-shell structure upconversion nanoparticles and core-shell structure upconversion nanoparticles under the excitation of a 980 nm laser. (The left shows non-core-shell structure upconversion nanoparticles and the right shows core-shell structure upconversion nanoparticles)
Figure 2:
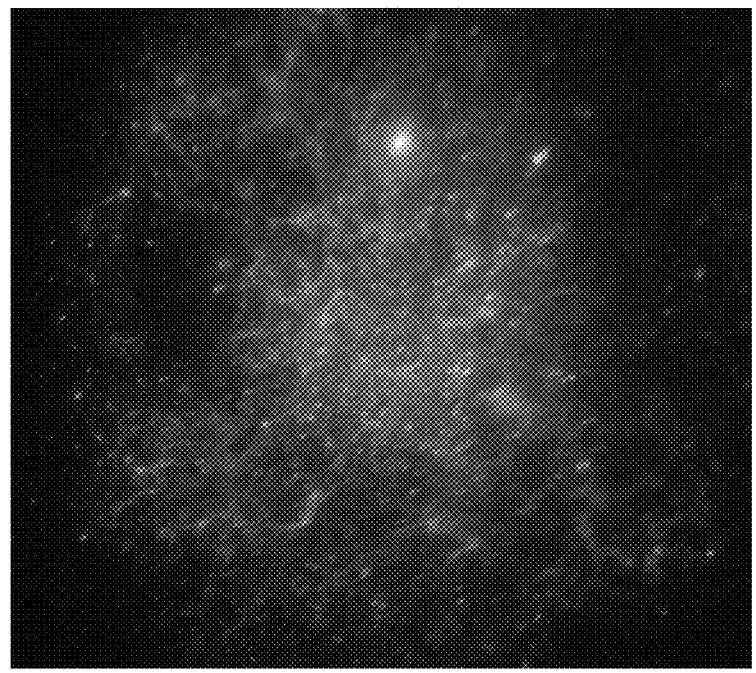
FIG. 2 shows a photofluorogram of flat board silk obtained in Example 1 under radiation of the 980 nm laser.

(1) Core-shell structure upconversion nanoparticles exciting green fluorescence ($\beta$-NaYF$_4$:Yb,Er@$\beta$-NaYF$_4$, diameter: about 50 nm) were prepared with a hydrothermal method, and subjected to surface PAA modification and grafted with concanavalin as a feeding material; and the synthetic method was as follows:

Core-shell structure upconversion nanoparticles ($\beta$-NaYF$_4$:Yb,Er@$\beta$-NaYF$_4$) were prepared with an existing method (J. Am. Chem. Soc. 128, 6426-6436.), and dispersed into a n-hexane solution. Polyacrylic acid (PAA) was grafted on the surface of nanoparticles by a ligand exchange method; 1 mL upconversion nanoparticle solution and 5 mL dimethyl formamide (DMF) were blended, and then 4 mL n-hexane was added for stirring for 3 h. 5-10 mL isopropanol was added for precipitation, and precipitates were washed by DMF for several times. The precipitates were resuspended in PAA/DMF solution (PAA concentration was 10 mg/mL, 5-10 mL), staying over the night, stirred, centrifuged and washed. 10 mg PAA-modified nanoparticles were taken and dispersed into 1 mL aqueous solution; 1 mg EDC and NHS were respectively added and stirred for reaction for 3-6 h, afterwards, 30 uL concanavalin aqueous solution (3-10 mg/mL) was added and stirred over the night, centrifuged and washed to obtain concanavalin-modified upconversion nanoparticles;

(2) the upconversion nanoparticles synthesized in the step (1) were dispersed uniformly with water to formulate a dispersion solution having a concentration of 2 g/L;

(3) mature mulberry leaves were picked and immersed into a nanoparticle aqueous solution in the step (2), 2 min later, fished out and dried naturally;

(4) silkworms were fed with the treated mulberry leaves in the step (3) after growing to the the third day of fifth-instar stage until spinning and silk cocooning;

(5) after growing to the spinning stage, silkworms were transferred to the smooth board surface and induced to spin on the flat board, then silk was collected;

(6) the obtained mulberry silk was irradiated by a 980 nm near-infrared laser, and the mulberry ilk on the flat board gives off bright green fluorescence (converted to a greyscale map, and the green fluorescence portion was partially converted to a greyish white portion), as shown in FIG. 2, thus obtaining a mulberry silk that fluoresces under near-infrared light.

Example 2

(1) Upconversion nanoparticles exciting red fluorescence (NaYF$_4$:1% Er, 1% Tm, a diameter: about 60 nm) were prepared with a hydrothermal method, and subjected to surface PAA modification and grafted with concanavalin as a feeding material; and the synthetic method was as follows:

Red fluorescent upconversion nanoparticles (NaYF$_4$:1% Er, 1% Tm) were prepared with an existing method (J. Phys. Chem. C, Vol. 113, No. 44, 2009), and dispersed into a n-hexane solution. Polyacrylic acid (PAA) was grafted on the surface of nanoparticles by a ligand exchange method; 1 mL upconversion nanoparticle solution and 5 mL dimethyl formamide (DMF) were blended, and then 4 mL n-hexane was added for stirring for 3 h. 5-10 mL isopropanol was added for precipitation, and precipitates were washed by DMF for several times. The precipitates were resuspended in PAA/DMF solution (PAA concentration was 10 mg/mL (5-10 mL), staying over the night, stirred, centrifuged and washed. 10 mg PAA-modified nanoparticles were taken and dispersed into 1 mL aqueous solution; 1 mg EDC and NHS were respectively added and stirred for reaction for 3-6 h, afterwards, 30 uL concanavalin aqueous solution (3-10 mg/mL) was added and stirred over the night, centrifuged and washed to obtain concanavalin-modified upconversion nanoparticles;

(2) the upconversion nanoparticles synthesized in the step (1) were dispersed uniformly with water to formulate a dispersion solution having a concentration of 5 g/L;

(3) mature mulberry leaves were picked and immersed into a nanoparticle aqueous solution in the step (2), 2 min later, fished out and dried naturally;

(4) silkworms were fed with the treated mulberry leaves in the step (3) after growing to the fifth-instar stage+3 d until spinning and silk cocooning;

(5) after silkworms spined silk cocoons, the silkworm cocoons were taken and subjected to reeling treatment to obtain mulberry silk giving off red fluorescence under the excitation of near-infrared light.

Example 3

(1) Core-shell structure upconversion nanoparticles (NaGdF$_4$:Yb/Er@NaGdF$_4$:Yb/Nd, a diameter: about 50 nm) exciting green fluorescence were prepared by a hydrothermal method, and subjected to surface PAA modification and grafted with concanavalin as a feeding material;

(2) the upconversion nanoparticles synthesized in the step (1) were dispersed uniformly with water to formulate a dispersion solution having a concentration of 5 g/L;

(3) mature mulberry leaves were picked and immersed into a nanoparticle aqueous solution in the step (2), 5 min later, fished out and dried naturally;

(4) silkworms were fed with the treated mulberry leaves in the step (3) after growing to the fifth-instar stage+3 d until spinning and silk cocooning;

(5) after silkworms spined silk cocoons, the silkworm cocoons were taken and subjected to reeling treatment to obtain mulberry silk giving off green fluorescence under the excitation of near-infrared light with a higher fluorescence intensity.

The mulberry silk prepared in the Example 3 served as a sample 1. Based on the method the same as that in Example 3, and the difference was that the dispersion solution in the step (2) was diluted by two concentrations to obtain a sample 2; a sample 3 was mulberry silk obtained by feeding common mulberry leaves; ICP-MS was used for quantitative analysis on the content of rare earth elements in mulberry silk. In comparison to the content of upconversion nanoparticles in conventional mulberry silk and modified mulberry silk, analysis and comparison are shown in Table 1.

Table 1 is a comparison table of the content of rare earth elements between the common mulberry silk and modified mulberry silk measured by ICP-MS in Example 3.

| 序号 | Element content | Y (%) | Er (%) | Yb (%) | Na (%) |
|---|---|---|---|---|---|
| 1 | Sample 1 | $2.0 \times 10^{-4}$ | $6.5 \times 10^{-4}$ | $5.0 \times 10^{-4}$ | 6.37 |
| 2 | Sample 2 | $5.1 \times 10^{-4}$ | $3.0 \times 10^{-4}$ | $1.49 \times 10^{-3}$ | 9.0 |
| 3 | Sample 3 | $3.3 \times 10^{-6}$ | $7.3 \times 10^{-6}$ | $6.7 \times 10^{-6}$ | 6.8 |

Table 1 indicates that the nanoparticles added herein can be used for the content detection in the final silk, indicating a higher feeding efficiency.

Finally, it should be noted that the above examples are merely detailed embodiments of the present invention. Apparently, the present invention is not limited to the above examples, and there are lots of transformations. A person skilled in the art can directly derive or associate with all the transformations from the disclosure of the present invention, and these transformations should be regarded within the protection scope of the present invention.

What is claimed is:

1. A preparation method for constructing fluorescent bombyx mori silkworm silk irradiated by near-infrared light and its products, comprising the following steps:
   (1) preparing upconversion nanoparticles, and performing surface modification with concanavalin to obtain modified upconversion nanoparticles;
   (2) uniformly dispersing the modified upconversion nanoparticles in the step (1) into water to formulate an aqueous solution of the upconversion nanoparticles;
   (3) picking mulberry leaves, immersing the mulberry leaves in the aqueous solution system of the nanoparticles in the step (2), draining the water, and drying the mulberry leaves;
   (4) after silkworms have grown for a time, feeding the treated mulberry leaves in the step (3) to the silkworms until the silkworms spin silk cocoons; and
   (5) collecting the silk fiber to obtain *Bombyx mori* silkworm silk that fluoresces under near-infrared light.

2. The preparation method for *Bombyx mori* silkworm silk that fluoresces under near-infrared light according to claim 1, wherein the upconversion nanoparticles have a core-shell structure.

3. The preparation method for fluorescent silk irradiated by near-infrared light according to claim 1, wherein the upconversion nanoparticles comprise one or more of $\beta$-NaYF$_4$:Yb, Er@$\beta$-NaYF$_4$ upconversion nanoparticles, NaGdF$_4$:Yb/Er@NaGdF$_4$:Yb/Nd, NaYF4:Yb/Er or upconversion nanoparticles emitting red fluorescence.

4. The preparation method for fluoescent silk irradiated by near-infrared light according to claim 1, wherein the upconversion nanoparticles are polyacrylic acid (PAA)-modified core-shell structure upconversion nanoparticles.

5. The preparation method for fluorescent silk irradiated by near-infrared light according to claim 1, wherein the preparation method of the upconversion nanoparticles is as follows: preparing the PPA-modified core-shell structure upconversion nanoparticles, and introducing concanavalin, then grafting the concanavalin on the surface of the upconversion nanoparticles by means of a cross-linking agent 1-ethyl-3-(3-dimethylaminopropyl)-carbodiimide (EDC) to form a composite co-polymer.

6. The preparation method for fluorescent silk irradiated by near-infrared light according to claim 1, wherein the method for surface modification with concanavalin is as follows: performing PAA grafting on the surface of the upconversion nanoparticles by an ligand exchange method, and performing centrifugation to obtain a precipitate; taking 10 mg PPA-modified nanoparticles and dispersing into 1 mL aqueous solution, and respectively adding 1 mg EDC and N-hydroxysuccinimide (NHS) and stirring for reaction for 3-6 h, then adding 30 μL concanavalin aqueous solution, wherein the concanavalin aqueous solution has a concentration of 3-10 mg/mL, then stirring the solution over night, and performing centrifugal washing to obtain the concanavalin-modified upconversion nanoparticles.

7. The preparation method for fluorescent silk irradiated by near-infrared light according to claim 1, wherein the aqueous solution of the upconversion nanoparticles has a concentration of 1-5 g/L.

8. The preparation method for fluorescent silk irradiated by near-infrared light according to claim 1, wherein silkworms are fed with the mulberry leaves in the step (3) after growing to the third day of fifth-instar stage.

9. The preparation method for fluorescent silk irradiated by near-infrared light according to claim 1, wherein the modified upconversion nanoparticles obtained in the step (1) have a mean diameter of 50-100 nm.

10. The preparation method for fluorescent silk irradiated by near-infrared light according to claim 1, wherein in step (3), the immersion time of the mulberry leaves is 2-5 min.

11. The preparation method for fluorescent silk irradiated by near-infrared light according to claim 1, wherein in step (5), silkworms are made to spin on a flat board, thus collecting silk.

12. A *Bombyx mori* silkworm silk that fluoresces under near-infrared light, wherein the mulberry silk is obtained by a method comprising:
   (1) preparing upconversion nanoparticles, and performing surface modification with concanavalin to obtain modified upconversion nanoparticles;
   (2) uniformly dispersing the modified upconversion nanoparticles in the step (1) into water to formulate an aqueous solution of the upconversion nanoparticles;
   (3) picking mulberry leaves, immersing the mulberry leaves in the aqueous solution system of the nanoparticles in the step (2), draining the water, and drying the mulberry leaves;
   (4) after silkworms have grown for a time, feeding the treated mulberry leaves in the step (3) to the silkworms until the silkworms spin silk cocoons; and
   (5) collecting the silk fiber to obtain *Bombyx mori* silkworm silk that fluoresces under near-infrared light.

\* \* \* \* \*